US010656165B2

(12) United States Patent
Kulkarni

(10) Patent No.: US 10,656,165 B2
(45) Date of Patent: May 19, 2020

(54) IN VITRO PROCESS FOR THE QUANTIFICATION OF CARBOXYMETHYL AND CARBOXYETHYL LEVEL OF ALBUMIN IN A SAMPLE

(71) Applicant: Council of Scientific & Industrial Research, New Delhi (IN)

(72) Inventor: Mahesh Jagdishrao Kulkarni, Pune (IN)

(73) Assignee: Council of Scientific & Industrial Research (IN)

( * ) Notice: Subject to any disclaimer, the term of this patent is extended or adjusted under 35 U.S.C. 154(b) by 367 days.

(21) Appl. No.: 15/019,656

(22) Filed: Feb. 9, 2016

(65) Prior Publication Data

US 2017/0168068 A1   Jun. 15, 2017

(30) Foreign Application Priority Data

Dec. 11, 2015   (IN) .......................... 4058/DEL/2015

(51) Int. Cl.
| | | |
|---|---|---|
| *G01N 33/68* | (2006.01) | |
| *A61B 10/00* | (2006.01) | |
| *A61K 38/38* | (2006.01) | |

(52) U.S. Cl.
CPC ..... *G01N 33/6893* (2013.01); *A61B 10/0045* (2013.01); *G01N 33/6851* (2013.01); *G01N 2333/765* (2013.01); *G01N 2440/38* (2013.01); *G01N 2560/00* (2013.01); *G01N 2800/042* (2013.01)

(58) Field of Classification Search
CPC .......... A61B 10/0045; G01N 33/6851; G01N 33/6893; G01N 2333/765; G01N 2440/38; G01N 2560/00; G01N 2800/042
See application file for complete search history.

(56) References Cited

U.S. PATENT DOCUMENTS 4,890,627 A * 1/1990 Haber ................ A61B 5/15003
600/578

OTHER PUBLICATIONS

Radin MS., "Pitfalls in Hemoglobin A1c Measurement: When Results May Be Misleading," Journal of General Internal Medicine, Feb. 2014; 29(2), pp. 388-394.
Hashimoto et al., "A1C But Not Serum Glycated Albumin Is Elevated Because of Iron Deficiency in Late Pregnancy in Diabetic Women," Diabetes Care Mar. 2010, vol. 33, No. 3, pp. 509-511.
Juraschek et al., "Alternative Markers of Hyperglycemia and Risk of Diabetes," Diabetes Care, Nov. 2012, vol. 35, pp. 2265-2270.
Bhonsle, et al., "Low Plasma Albumin Levels Are Associated with Increased Plasma Protein Glycation and HbA1c in Diabetes," Journal of Proteome Research, Feb. 3, 2012, vol. 11, pp. 1391-1396.

(Continued)

*Primary Examiner* — Jeremy C Flinders
(74) *Attorney, Agent, or Firm* — Lerner, David, Littenberg, Krumholz & Mentlik, LLP

(57) ABSTRACT

An in vitro method for the identification and quantification of glycated human serum albumin to assess the extent of diabetic complications in diseased individuals. Further, a diagnostic kit for identifying the extent of diabetes in a diseased individual by estimating glycated serum albumin levels in such individuals.

5 Claims, 5 Drawing Sheets

Specification includes a Sequence Listing.

(56) References Cited

OTHER PUBLICATIONS

Manigrasso et al., "Unlocking the Biology of RAGE in Diabetic Microvascular Complications," Trends Endocrinol Metab., Jan. 2014; 25(1), pp. 1-18.
Thornalley et al., "Quantitative Screening of Advanced Glycation Endproducts in Cellular and Extracellular Proteins by Tandem Mass Spectrometry," Biochem J., Nov. 1, 2003, vol. 375, pp. 581-592.
Zhang et al., "Comprehensive Identification of Glycated Peptides and Their Glycation Motifs in Plasma and Erythrocytes of Control and Diabetic Subjects," Journal of Proteome Research, Jul. 1, 2011, vol. 10, Issue 7, pp. 3076-3088.
Zhang et al., "A New Strategy for Early Diagnosis of Type 2 Diabetes by Standard-Free, Label-Free LC-MS/MS Quantification of Glycated Peptides," Diabetes, Nov. 2013, vol. 62, pp. 3936-3942.
Greifenhagen et al., "Sensitive and Site-Specific Identification of Carboxymethylated and Carboxyethylated Peptides in Tryptic Digests of Proteins and Human Plasma," Journal of Proteome Research, Feb. 6, 2015, vol. 14, issue 2, pp. 768-777.
Bhonsle et al., "'Zoom-In'—A targeted database search for identification of glycation modifications analyzed by untargeted tandem mass spectrometry," Eur. J. Mass. Spectrom., Dec. 4, 2012, vol. 18, pp. 475-481.
Walsh et al., "Bluues server: electrostatic properties of wild-type and mutated protein structures," Bioinformatics, Jun. 2012, vol. 28, No. 16, pp. 2189-2190.

\* cited by examiner

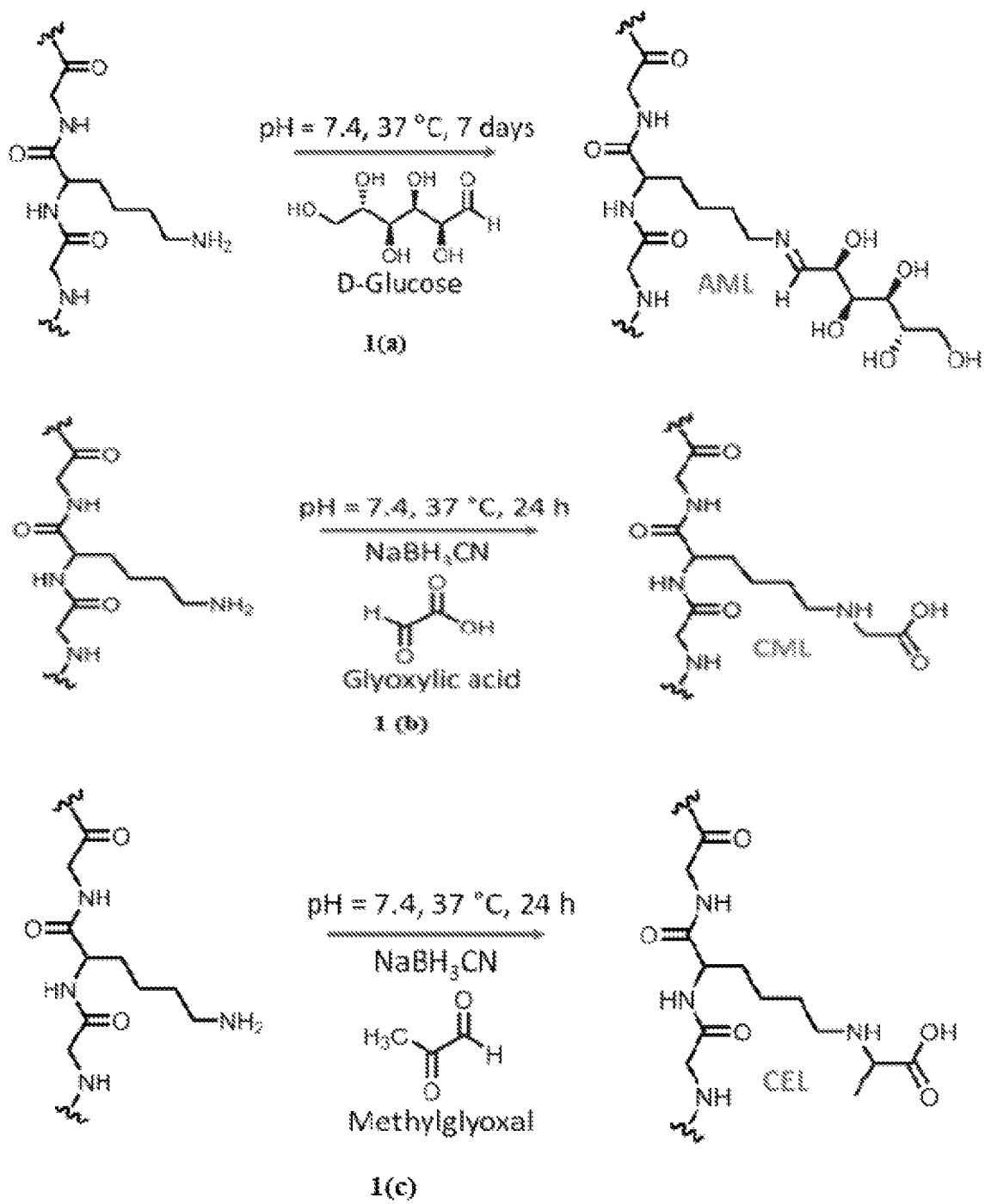
Figure 4 depicting the conversion of Human serum albumin into AGE modified HSA.

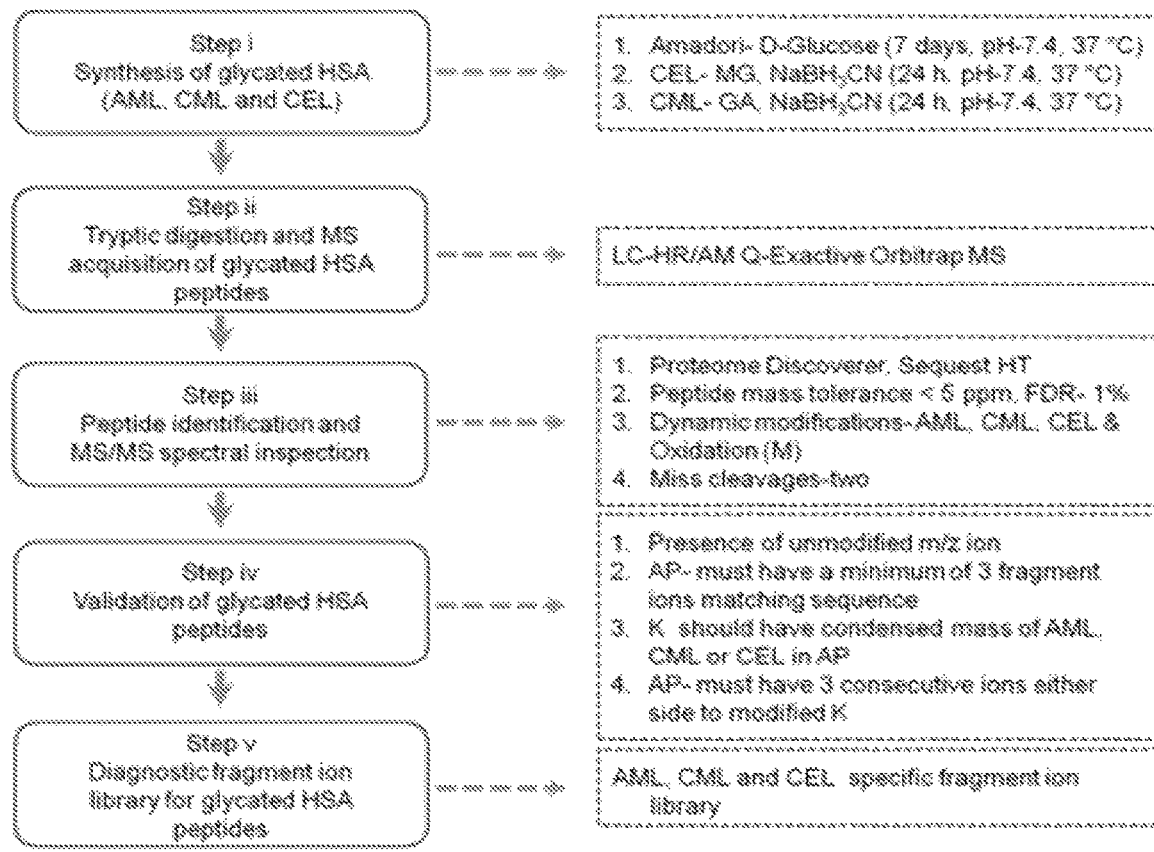
Figure 5 depicting the procedural order of the construction of the diagnostic ion library and further illustrates the four major stages of ion library construction.

IN VITRO PROCESS FOR THE QUANTIFICATION OF CARBOXYMETHYL AND CARBOXYETHYL LEVEL OF ALBUMIN IN A SAMPLE

FIELD OF THE INVENTION

The present invention relates to an in vitro process for the quantification of carboxymethyl and carboxyethyl level of albumin. In particular, the present invention relates to a method for the identification and quantification of glycated human serum albumin level. Further, the present invention relates to a diagnostic kit for the quantification of glycated human serum albumin.

BACKGROUND AND PRIOR ART OF THE INVENTION

Diabetes is characterized by prolonged hyperglycaemic conditions resulting from pancreatic dysfunctions thereby causing deficiencies in insulin secretion, insulin action, or both and leading to abnormalities in carbohydrate, fat, and protein metabolism. One of the several consequences of elevated plasma glucose levels in diabetics is enhanced protein glycation. Glycation involves non-enzymatic addition of reducing sugars and/or their reactive degradation products to amine groups on proteins. This process is stimulated by the presence of elevated blood glucose concentrations in diabetes and occurs with various proteins including human serum albumin (HSA). Human serum albumin is an abundant plasma protein present in concentrations ranging from 30-50 g/L and accounts for approximately 60% of the total protein content in serum.

Biomarkers associated with diabetes are mainly based on protein glycation e.g. glycated hemoglobin (HbA1c), fructosamine and glycated albumin. HbA1c is considered as a 'gold standard' marker reflecting the glycemic status of a diabetic over a period of 90-120 days. Although many studies have suggested the usefulness of HbA1c, factors such as anaemia, blood loss, splenomegaly, iron deficiency can cause severe fluctuations in levels of HbA1c (Radin M S. *J Gen Intern Med* 2014; 29:388-94). In view of HbA1c level being influenced by haemodialysis, hemoglobin level, and erythropoietin dose, glycated albumin levels could be a more reliable indicator of glycemic level in diabetics and in patients on hemodialysis who have diabetes and anuria than HbA1c level. Alternatively, glycated albumin has also been proposed as a glycemic biomarker, as it reflects short-term changes in glucose levels, and has been strongly recommended for gestational diabetes (Hashimoto K et al, *Diabetes Care* 2010; 33:509-11). Juraschek S P, et al (*Diabetes Care* 2012; 35:2265-70) and Bhonsle H S, et al (*J Proteome Res* 2012; 11:1391-6) have studied positive correlation between increased levels of glycated albumin and hyperglycaemia.

Additionally, several recent studies have suggested that levels of glycated albumin are associated with pre-diabetic conditions/symptoms, and microalbuminuria. Thus, the quantification of glycated albumin is of appreciable clinical significance.

Human serum albumin readily undergoes glycation contributing mainly to increased levels of advanced glycation end-products in plasma, thus glycated albumin has been suggested as an additional marker for monitoring the glycemic status. Several studies have implicated AGE's in the development of insulin resistance, as well as in pathogenesis of diabetic complications (Manigrasso M B et al, *Trends Endocrin Met* 2014; 25:15-22). Certain lysine residues of HSA are more prone to undergo glycation modification, these are also referred to as glycation/glucose sensitive sites (Thornalley, P. J., et al (2003) *Biochem J* 375, 581-592). Since these lysine residues are constantly exposed to higher glucose concentration; the specific sites can undergo sequential AGE modifications followed by initial Amadori rearrangement. Further, CML and CEL constitute around 80% percent of total AGE's. The levels of AGEs increase substantially in diabetic plasma due to hyperglycemic condition. Therefore, analysis of plasma AGEs can possibly provide information about the severity of diabetes.

Prevalent quantification techniques are restricted to estimate Amadori modified lysine (AML) peptides of albumin, however there has been no method devised to quantify levels of predominant AGE modified peptides such as carboxymethyl lysine (CML) and carboxyethyl lysine (CEL) peptides of albumin which are required to be quantified in diabetics to gauge the extent of damage and complications arisen by the disease.

Methods reported to quantify AGE modified albumin by various approaches include colorimetric assay, ketoamine oxidase assay, enzyme-linked boronate immunoassay, fluorescence spectroscopy, boronic acid affinity chromatography assay and mass spectrometry (MS). Amongst these approaches, MS offers precise characterization of protein glycation including the amino acid involved in the modification. AML modification has been extensively studied by different MS approaches. The fragmentation pattern and diagnostic ions for AML rearrangement product has been well established.

Diagnostic ions serve as the most reliable way of identifying glycated peptide by tandem mass spectrometry. Thus, having a good MS/MS fragment ions is key for precise characterization of glycation. However, the ratio of in vivo AGE modified to unmodified protein is significantly low, which limits better MS/MS. Further, Zhang Q B, et al (*J Proteome Res* 2011; 10:3076-88) by using a combination of immune-depletion, enrichment and fractionation strategies, have identified a total of 7749 unique glycated peptides corresponding to 1095 native human plasma proteins, 1592 in vitro glycated human plasma proteins and 1664 erythrocyte proteins.

Stable-isotope-dilution tandem mass spectrometry method has also been employed for simultaneous analysis of CML and CEL in hydrolysates of plasma proteins and $^{13}C_6$-glucose to quantify glycated proteins in the plasma and erythrocytes. In a recent study, the glycation sensitive peptides of HSA that could serve as markers for early diagnosis of type 2 diabetes were quantified by using MS based $^{18}O$-labeling technique (Zhang M et al, *Diabetes* 2013; 62:3936-42). However, most of the previous studies have focused on AML modification, than other AGE modification. Therefore, there arises a need for the development of MS/MS fragment ion library for quantification of AML, CML and CEL modifications of albumin.

Hoffmann R et al in a research study published in *J Proteome Res.* 2015 Feb. 6; 14(2): 768-77 reported characteristic fragmentation patterns of CML- and CEL-containing peptides and two modification-specific reporter ions for each modification. The process employed allowed sensitive and selective precursor ion scans to detect modified peptides in complex sample mixtures. Even though, this study teaches the CML modified sites in different proteins, including modified lysine residues 88 and 396 of human serum albumin, there is no attempt to identify specific modified peptides in any particular stage of diabetes. Moreover, glycation is chronic process; a given protein can undergo dynamic heterogeneous transformations as they have varying biological life span influencing the function of a protein. Thus, to assess the degree of glycation at a given pathophysiological condition, precise identification of glycation becomes critical.

Since there is a pending need in the art to understand AGE site specific modification in albumin and keeping in mind the clinical significance of AGE-HSA quantification, the present inventors have devised a method for identifying and quantifying diagnostic peptide markers specific to AGE modified human serum albumin, mainly carboxymethyl and carboxyethyl lysine residues.

Embodiments of the Invention

An embodiment of the present invention is to provide a process for the identification and quantification of Advanced Glycation end-products (AGE) modified human serum albumin (HSA) to assess the extent of diabetic complications in diseased individuals.

Another embodiment of the present invention is to provide a process for the quantification of AGE modified i.e. deoxyfructosyl, carboxymethyl or carboxyethyl modified peptides of human serum albumin to indicate the stage of diabetes i.e. microalbuminuria, pre-diabetic, diabetic, and poorly controlled diabetes.

Yet another embodiment of the present invention is to provide a diagnostic kit to evaluate the etiology of diabetic complications by estimating the glycated level content in human serum albumin.

SUMMARY OF THE INVENTION

The present invention provides an in vitro process for identifying and quantifying glycated level of albumin in a sample comprising;
(a) subjecting the biological fluid to mass spectrometry to generate fragment ions;
(b) identifying the specificity of fragment ions obtained in step (a) to advanced glycation end-product (AGE) modified glycation sites selected from deoxyfructosyl, carboxymethyl and carboxyethyl modified amino acid residues in human serum albumin by comparing the said fragment ions with signature ions in the diagnostic fragment ion library; and
(c) further quantifying the AGE modified peptide content wherein AGE modified glycation sites are situated at lysine and valine residues.

In an aspect, the present invention provides a fragment ion library comprising fragment ions specific to AML, CML and CEL modified peptides of the synthetically modified albumin established using high resolution accurate mass spectrometry.

The modified peptides were manually inspected and validated for their modification. Further the fragment ion library was used for targeted quantification of glycated peptides of albumin in the context of diabetes. Targeted mass spectrometric analysis leads to the identification and quantification of 13 glycated peptides comprising of 4 AML, 7 CML and 2 CEL modification representing 9 lysine sites of albumin. Five glycated lysine sites namely K549, K438, K490, K88 and K375 were observed to be highly sensitive for glycation modification as their respective m/z intensity showed maximum fold change.

In yet another aspect, the present invention provides a diagnostic kit for identification and quantification of AGE modified glycated human serum albumin level content comprising:

(a) a sterilized device, preferably minimally invasive, to draw out serum from a subject wherein the serum is to be subjected to fragmentation by mass spectrometry methods;
(b) a chart, figure or representation of the signature fragment ion library specific to each glycated peptide; and
(c) a catalogue or product information sheet containing instructions for use of the kit.

BRIEF DESCRIPTION OF FIGURES

FIG. 4 depicts the conversion of Human serum albumin into AGE modified HAS.

FIG. 5 depicts the procedural order of the construction of the diagnostic ion library and further illustrates the four major stages of ion library construction.

DETAILED DESCRIPTION OF THE INVENTION

Figure 1:
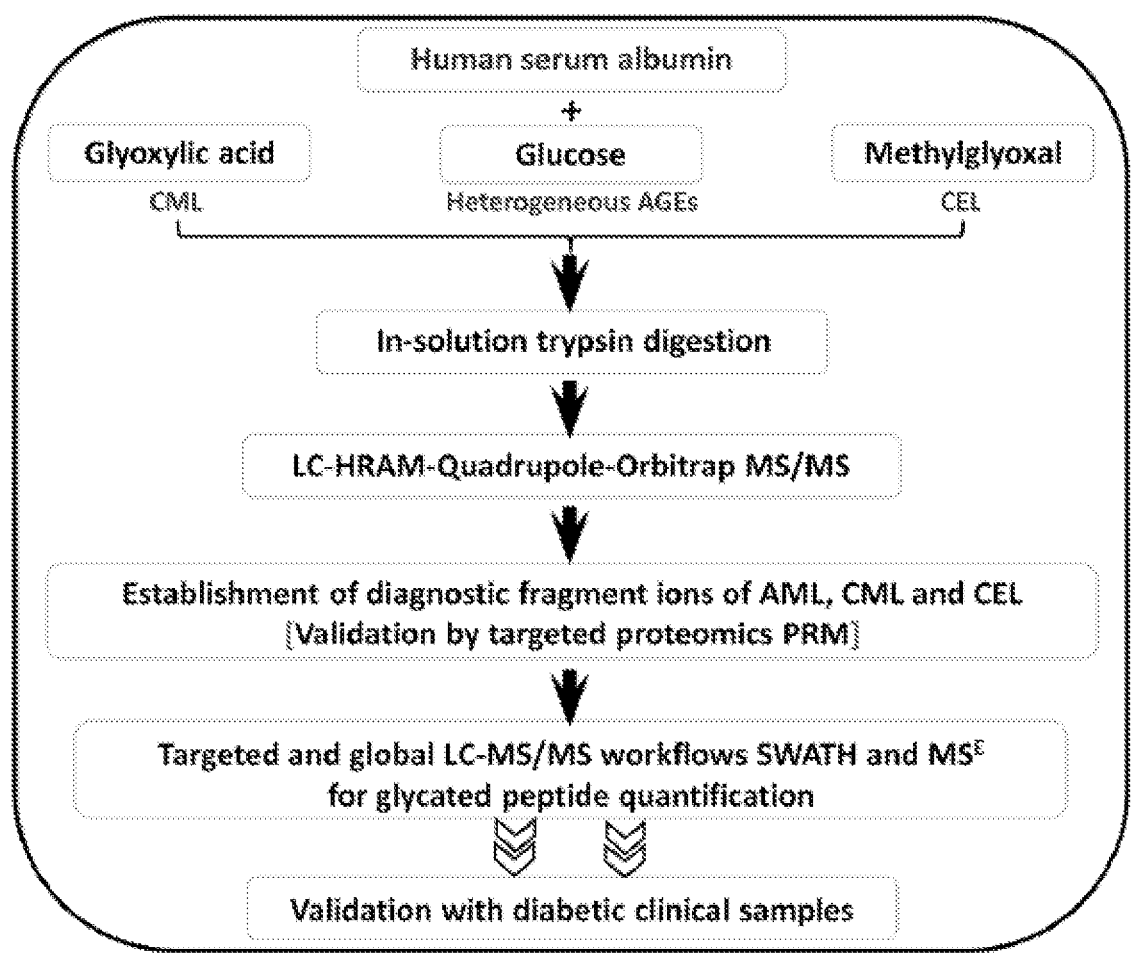
FIG. 1 depicts the overview design of establishing a diagnostic library, peptide quantification and validation with diabetic clinical plasma sample.

The invention will now be described in detail in connection with certain preferred and optional embodiments, so that various aspects thereof may be more fully understood and appreciated.

The present invention provides a process for identifying and quantifying glycated level of albumin in human serum comprising;
(a) subjecting human serum sample to mass spectrometry to generate fragment ions;
(b) identifying the specificity of fragment ions obtained in step (a) to advanced glycation end-product (AGE) modified glycation sites selected from deoxyfructosyl, carboxymethyl and carboxyethyl modified amino acid residues in human serum albumin by comparing the said fragment ions with signature ions in the diagnostic fragment ion library; and
(c) further quantifying the AGE modified peptide content wherein AGE modified glycation sites are situated at lysine and valine residues.

In line with the above, the method to identify glycated peptides and quantify the glycemic status in individuals diagnosed with diabetes involves subjecting a human serum sample to fragmentation to generate diagnostic fragment ions. This fragmentation is brought about by mass spectrometry methods. The fragment ions resulting from the given biological fluid are determined for their specificity with deoxyfructosyl, carboxymethyl and carboxyethyl modified amino acid residues in human serum albumin, by comparing the said ions with the ions in a diagnostic ion library. A reference may be made to Table 1 of the present invention containing the said diagnostic fragment ions specific to standard glycated peptide sites.

Finally, the glycated albumin sites are quantified by target based mass spectrometry methods, by which the extent of diabetes and its associated complications in a diabetic or a person exhibiting hyperglycaemic symptoms can be assessed. The % carboxymethylated and carboxyethylated serum albumin levels is estimated by MRM (Multiple reaction monitoring)/PRM (Parallel reaction monitoring)/ SWATH (Sequential Window Acquisition of all Theoretical Fragment Ion Spectra)/$MS^E$ methods.

Accordingly, the AGE modification of human serum albumin (HSA) is depicted in FIG. 4. In a subject diagnosed with diabetes or a person exhibiting symptoms of diabetes the serum albumin is modified in the presence of elevated levels of glucose or Glyoxylic acid (GA) or Methyl Glyoxal (MG) to obtain Amadori or deoxyfructosyl modified lysine (AML), carboxymethyl modified lysine (CML) and carboxyethyl modified lysine (CEL) peptides respectively.

In the present specification Amadori modified lysine i.e. AML and deoxyfructosyl modified lysine refer to the same modification and may be used interchangeably.

The levels of these AGE modified peptides have been quantified employing the present method. The glycated sites are represented in Seq Id No. 1 i.e. the amino acid sequence representing human serum albumin Glycated protein sequences having 80% similarity with Seq Id No. 1 are quantified by employing the present method.

In an embodiment, the present invention provides for the identification, characterization and quantification of thirteen glycated peptides in diabetic plasma comprising four AML modified residues, seven CML modified residues and two CEL modified residues representing nine lysine (K) sites of albumin.

In the present application, in accordance with the standard alphabetic letters used to represent amino acids, the alphabet K referred to in the following embodiments represents the amino acid lysine.

In another preferred embodiment, the present invention provides for the identification and quantification of AGE glycated sites of Seq Id No. 1 selected from the group consisting of K36, K88, K160, K161, K183, K375, K438, K490 and K549.

In yet another preferred embodiment, the present invention provides highly sensitive glycation modification sites of amadori or deoxyfructosyl modified or carboxymethyl lysine modified sites selected from the group consisting of K549, K438, K490, K88 and K375 of SEQ ID No. 1.

Figure 2:
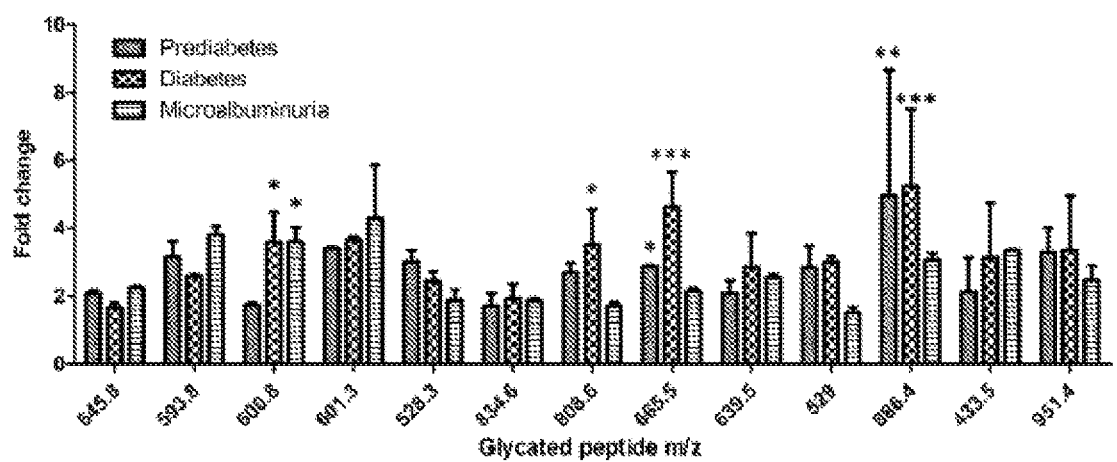
FIG. 2 depicts glycated peptide ion fold change significance analysis by two-way ANOVA among disease conditions viz. prediabetes, diabetes and microalbuminuria (SWATH) workflow). Significant difference in data at $p<0.0001$ (indicated by **), at $p<0.001$ (indicated by *), at $p<0.01$ (indicated by **), at $p<0.05$ (indicated by *)
Figure 3:
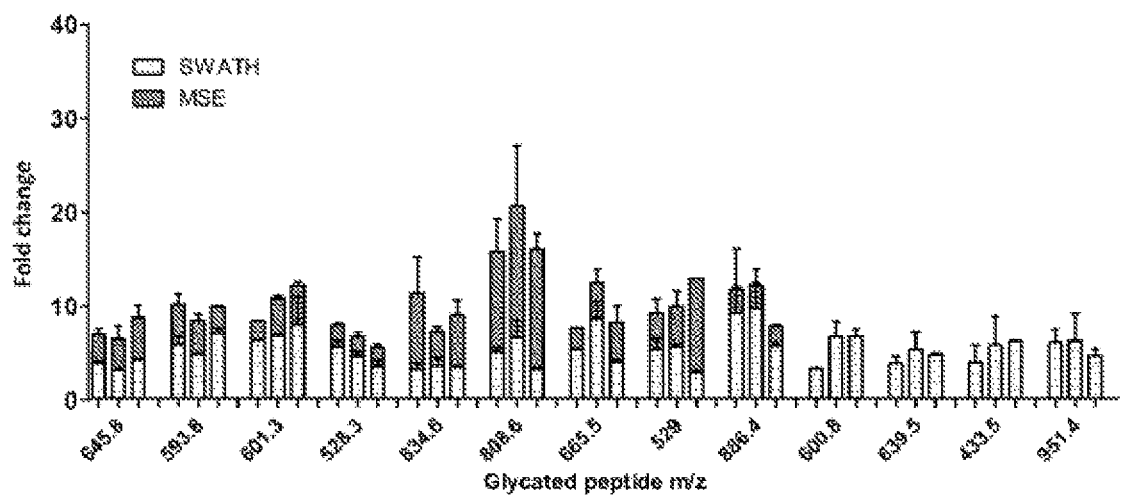
FIG. 3 depicts comparisons of intensity fold change of glycated peptide ion quantified by both SWATH and $MS^E$ workflow.

On performing SWATH analysis, the fold change of the peptides were analysed. Their glycated sites selected from K549, K438, K490, K88 and K375 of Seq Id No. 1 were determined to have maximum fold change depending on their respective m/z intensities (FIGS. 2 and 3).

Accordingly, the aforementioned sites have both AML and CML modifications, and position K549 of SEQ ID No. 1 has an additional CEL modification. K375 (m/z 886.4) showed the highest significant fold change in prediabetes and diabetic plasma. Although it is intriguing that only one lysine site i.e. K549 was found to be CEL modified, this result strongly supports previous studies where no CEL modified peptide was identified. FIG. 6 indicates an increase in fold change across glycated peptide m/z values. At m/z 808.6, an increased ion fold change is observed in diabetic conditions, thereby indicating the significant glycation at K490 in diabetic conditions.

Precursor ions appertaining to K549, K438, K490, K88, K549 were defined to serve as potential novel markers for assessing the degree of glycation or diabetic glycaemic status in general and
m/z 645.8 ($K^{AML}$*QTALVELVK), m/z 593.8 ($K^{CML}$*QTALVELVK), m/z 600.8 ($K^{CEL}$*QTALVELVK), m/z 601.3 ($K^{AML}$*VPQVSTPTLVEVSR), m/z 528.3 ($K^{CML}$*VPQVSTPTLVEVSRNLGK),
m/z 834.6 (MPC*AEDYLSVVLNQLC*VLHEK$^{AML}$*TPVSDR),
m/z 808.6 (MPC*AEDYLSVVLNQLC*VLHEK$^{CML}$*TPVSDR),
m/z 665.5 (TC*VADESAENC*DK$^{AML}$*SLHTLFGDK),
m/z 639.5 (TC*VADESAENC*DK$^{CML}$*SLHTLFGDK),
m/z 886.4 (QNC*ELFEQLGEYK$^{CML}$*FQNALLVR) in particular.

In another embodiment, the present invention provides a diagnostic ion library comprising fragment ions specific to deoxyfructosyl, carboxymethyl and carboxyethyl modified glycation sites in human serum albumin.

This present diagnostic ion library is used for quantification of AGE modified peptides of albumin by targeted mass spectrometric approaches. The process for establishing the diagnostic ion library is shown in FIG. 1.

In yet another embodiment, the present invention provides quantification of AGE modified peptides of human serum albumin by targeted SWATH workflow in clinical plasma to evaluate their use as diagnostic peptides.

In a preferred embodiment, the present invention provides a diagnostic kit for the identification and quantification of AGE modified glycated human serum level content comprising:
 (a) a sterilized device, preferably minimally invasive, to draw out serum from the diseased individual, which is to be subjected to fragmentation by mass spectrometry methods;
 (b) a chart, figure or representation of the signature fragment ion library specific to each glycated peptide; and
 (c) a catalogue or product information sheet containing instructions for use of the kit.

Accordingly, the method of employing the present diagnostic kit involves subjecting the human serum sample to fragmentation to generate diagnostic fragment ions. This fragmentation is brought about by target based mass spectrometry methods. The fragment ions resulting from the given biological fluid are determined for their specificity with deoxyfructosyl, carboxymethyl and carboxyethyl modified amino acid residues in human serum albumin, by comparing the said ions with the ions present in the diagnostic ion library. A reference is made by the subject or a pathologist to a chart, figure or representation containing the signature diagnostic fragment ions specific to standard glycated peptide sites accompanying the diagnostic kit, and the concentration of glycated peptides is quantified by mass spectrometric methods. The extent of diabetes is thus assessed using the present diagnostic kit.

In an embodiment, the present invention provides the use of the diagnostic kit in identifying the extent of diabetic complications in a subject, by classifying the diabetic stage to be pre-diabetic, current diabetic stage and also in the diagnosis of microalbuminuria in the said subject.

The following examples, which include preferred embodiments, will serve to illustrate the practice of this invention, it being understood that the particulars shown are by way of example and for purpose of illustrative discussion of preferred embodiments of the invention.

EXAMPLES

Example 1

Establishment of Diagnostic Fragment Ion Library for AML, CML and CEL Peptides of Human Serum Albumin The present fragment ion library was constructed sequentially in five stages as depicted in FIG. 5. (i) human serum albumin was modified with glucose or Glyoxylic acid(GA) or Methyl Glyoxal (MG) to obtain Amadori or deoxyfructosyl modified lysine (AML), carboxymethyl lysine (CML) and carboxyethyl lysine (CEL) modified peptides respectively (Scheme 1), (ii) the AGE modified HSA obtained in step (i) were subjected to tryptic digestion and peptides formed were analyzed by using high resolution accurate mass spectrometer (Q Exactive Hybrid QuadrapoleOrbitrap Miss.), (iii) manually validating the peptides for consensus MS and MS/MS spectra, (iv) constructing the final diagnostic fragment ion library for AML, CML and CEL peptides of albumin (Table 1).

Example 2

Validation of Glycated Peptides of Human Serum Albumin by MS/MS Spectrum

The search algorithm used by Korwar A M et al (*Eur J Mass Spectrom* 2012; 18:475-81) was employed to identify glycated peptides which were manually validated by inspecting each MS/MS spectrum. Accordingly, at MS, each AGE modified peptide precursor was reviewed for the presence of unmodified peptide precursor ion.

CML modified precursor ion m/z 566.6 (1697.9 Da MH$^+$) corresponding to peptide (K*VPQVSTPTLVEVSR) was inspected for the presence of its unmodified precursor ion m/z 547.31 (1639.9 Da). Such manual interrogation was performed for all glycated peptide precursor ions having an increased mass of 162.053, 58.005 and 72.021 Da corresponding to AML, CML and CEL modifications respectively. At MS/MS, glycated precursor fragment ions were carefully evaluated for glycated lysine ions of m/z 291.14 [128.09+162.051], m/z 187.09 [128.09+58.005], m/z 201.11 [128.09+72.021] corresponding to AML, CML and CEL respectively, followed by increment shift in mass across b or y ion series depending on the site of modification in peptide.

Example of modification at N-terminal lysine, CML modified K*VPQVSTPTLVEVSR (m/z—566.652) peptide spawned signature diagnostic b series fragment ions $b_1^+$—187.10, $b_2^+$—286.17, $b_3^+$—383.22, $b_4^+$—511.28, $b_5^+$—610.35, $b_6^+$—697.38, $b_7^+$—798.43, $b_9^+$—996.53 bearing 58 Da mass shift across b ion series.

Example of modifications at C-terminal, CML modified RHPYFYAPELLFFAK*R (m/z—705.037) peptide spawned signature diagnostic y series fragment ions $y_2^+$—361.21, $y_3^+$—432.25, $y_4^+$—579.32, $y_5^+$—726.39, $y_6^+$—839.47, $y_7^+$—952.56, $y_8^+$—1081.60, $y_9^+$—1178.65 and $y_{10}^+$—1249.69 bearing 58 Da mass shift across y ion series.

Example modification in the middle of the peptide, CML modified FGERAFK*AWAVAR (m/z—783.910) peptide spawned signature diagnostic fragment ions of both b and y series $b_7^+$—894.44, $b_8^+$—965.48, $b_9^{2+}$—576.28, $b_{10}^+$—1222.60, $b_{11}^+$—1321.66, $b_{12}^+$—1392.70, $y_7^+$—859.47, $y_8^+$—1006.54, $y_9^+$—1077.58, $y_{10}^{2+}$—617.34.

In certain instances, poor MS/MS techniques result in identification of false positives. Therefore to rule out any such identification, presence of three consecutive fragment ion bearing modification was adopted as an important criterion.

All such glucose, GA and MG induced glycated peptides are disclosed in Table 1 (Corresponding fragment ions and MS/MS spectra specific to the glycated peptides are not shown). In disagreement with the rule of consecutive ions, some of the peptides were consented as true modifications for their better MS/MS fragmentation pattern, where either y or b series ion were bearing the shift of modified mass, (related data not shown, as well as data related to corresponding peptide fragment ions and MS/MS spectra and corresponding un-glycated peptides is not produced in the present patent application).

Together 50 glycated peptides were identified for AML, CML and CEL modified HSA. Each of the glycated protein showed 20, 17, 13 modified peptides induced by glucose GA and MG respectively. These 50 modified peptides represented 23 lysine modified sites. K549, K438 and K183 sites were modified 6 times followed by K375, K490 (each 4 times) suggesting that these sites were more sensitive to glycation modification than others (Table 1). MS and corresponding XICs of all 50 glycated peptides along with unmodified control peptides were also performed.

The reliability of diagnostic fragment ion library for AML, CML and CEL modified peptides of HSA was validated by parallel reaction monitoring of selected glycated peptide ion m/z. The resultant ion chromatograms were extracted with a mass tolerance of 5 ppm and presence of at least 2 corresponding diagnostic fragment ions were confirmed manually.

Example 3

Validation of the Present Fragment Ion Library

Signature ions specific to glycated peptides determined by the present method of AGE quantification was validated by quantifying and validating the said glycated sites in human serum albumin in clinical plasma samples of healthy subjects and patients supposedly diagnosed having diabetes.

Accordingly, subjects were recruited from the Madras Diabetes Research Foundation (MDRF). The study was approved by the institutional ethics committee of MDRF and prior written informed consent was obtained from all the study subjects. Descriptive characters and diagnostic parameters including fasting blood glucose, HbA1c, oral glucose tolerance test, postprandial blood Sugar, lipids, urea, creatinine, and microalbumin were measured (data not shown). The plasma samples were classified into four group namely healthy control [Normal glucose tolerance (NGT)], prediabetes [impaired glucose tolerance (IGT)], diabetic[T2DM], microalbuminuria [MIC]. Two plasma samples with similar HbA1c (deviation of <0.2%) were pooled and three such pooled plasma in each group were used for mass spectrometric analysis.

First, The AGE-HSA MS/MS fragment ion library with diagnostic ions was established for glycation modifications AML, CML and CEL. Diagnostic signature ions were validated for glycated peptides in diabetic plasma using targeted parallel reaction monitoring (PRM) workflow. Further, based on the fragment ion library information, glycated peptides in healthy control, prediabetic, diabetic and microalbuminuria plasma were quantified by using SWATH to discover candidate peptide biomarkers to assess the extent of glycation in diabetes. The results of SWATH were verified by $MS^E$, another label free quantification method. Two-way analysis of variance (ANOVA) was performed to assess the statistical significance of quantified glycated peptides.

Example 4

Materials and Method Employed for Clinical Sample Preparation and Subsequent Analysis All the chemicals were procured from Sigma-Aldrich (Sigma-Aldrich, MO, USA). MS-grade solvents (acetonitrile (ACN), water, and methanol) were procured from J T. Baker (J T. Baker, Pa., USA). RapiGest was procured from Waters (Waters Corporation, MA, USA). Membrane filters of 3 and 30 KDa cut off were procured from Millipore (Millipore, Mass., USA).

Sample Preparation for MS Analysis

In-solution tryptic digestion: Equal amount of protein (100 μg) of AGE-modified HSA and clinical plasma proteins were diluted with 100 μL of ammonium bicarbonate buffer (50 mM) containing 0.1% RapiGest followed by incubation at 80° C. for complete proteome solubilization. The denatured proteins were then reduced with DTT (0.100 M) at 60° C. for 15 mM, followed by alkylation with iodoacetamide (0.200 M) at room temperature in the dark for 30 mM. The proteins were digested with proteomic grade trypsin at 1:50 enzyme to substrate ratio overnight at 37° C. The digestion reaction was stopped by adding concentrated HCL and incubated for 10 mM at 37° C. before centrifuged. The peptides were desalted by using C18 Zip tip (Millipore, Mass., USA) and concentrated by vacuum centrifuge and stored at −20° C. until further use.

Liquid Chromatography-Mass Spectrometric Analysis

Instrument-specific methods and settings [(LC-HR/AM Q-ExactiveOrbitrap and PRM), (Triple TOF 5600 (DDA and SWATH-MS), (label free LC-MSE on SYNAPT HDMS)] were used for the construction of fragment ion library and quantification of glycated peptides.

Structure Analysis

Three dimensional structure of albumin highlighting lysine residues image was generated by using PyMOL Molecular Graphics System (Schrodinger, LLC). Electrostatic surface potentials were calculated using Bluues with default values as implemented in the Bluues web server (Walsh I, et al Bioinformatics 2012; 28: 2189-90).

Statistical Analysis

Significant differences between glycated peptide m/z within disease condition and across m/z were determined by using two-way ANOVA followed by Tukey's multiple comparison test. NS represents non-significant difference within the conditions and/or across m/z.

Example 5

Quantification of HSA Glycated Peptides in Clinical Plasma

AGE modified HSA peptides from pooled plasma samples of healthy control, prediabetic, diabetic and microalbuminuria were quantified by using label-free targeted SWATH workflow. In SWATH analysis, the intensity fold change of 13 glycated peptides listed in FIG. 3 were found to be consistently higher in prediabetes, diabetes and microalbuminuria in comparison with the control.

Further two-way ANOVA was performed to assess the statistical significance of intensity fold change of glycated HSA peptides amongst prediabetes, diabetes and microalbuminuria. Two-way ANOVA results showed statistically significant interaction with a total variance of 29.63% at p, 0.0001 between glycated peptides m/z and different diabetic conditions (prediabetic, diabetic and microalbuminuria). Tukey's multiple comparisons test suggested that, out of 13 consistent glycated peptides, fold expression of four m/z viz. 600.8, 808.6, 665.5 and 886.4 was significant when compared across three diabetic conditions (i) m/z—600.8, Site—K549, sequence—K$^{CEL}$*QTALVELVK was found to be significant in diabetes (p=0.01) and microalbuminuria (p=0.02) as compared to prediabetes; (ii) m/z—808.6, Site—K490, sequence MPC*AEDYLSVVLNQLC*VLHEK$^{CML}$*TPVSDR was found to be significant in diabetes (p=0.01) as compared to prediabetes and microalbuminuria; (iii) m/z—665.5, Site—K88, sequence—TC*VADESAENC*DK$^{AML}$*SLHTLFGDK was found to be more significant in diabetes (p=0.0005) as compared to microalbuminuria and significant in prediabetes (p=0.03) as compared to microalbuminuria; (iv) m/z—886.4, Site—K426, sequence—QNC*ELFEQLGEYK$^{CML}$*FQNALLVR was found to be more significant in diabetes (p=0.0007) and prediabetes (p=0.003) as compared to microalbuminuria. Further, to determine the significance of intensity fold change of each glycated peptide was compared across all glycated peptides. Glycated peptide ion m/z 886.4 and m/z 433.5 were found to be significant in prediabetic; while m/z 886.4, m/z 433.5 and m/z 665.5 were found to be significant in diabetes; and m/z 601.3 and m/z 593.8 were found to be significant in microalbuminuria condition.

Further, the results of SWATH analysis were verified by MS$^E$ workflow. Out of 13 glycated peptides, 9 peptides intensity fold change was found to be higher in prediabetes, diabetes and microalbuminuria in comparison with control, and showed similar trend with the SWATH results (FIG. 3).

Example 6

Glycated Sites 3D Structures of Human Serum Albumin

In vitro glucose, GA and MG induced glycated HSA representing glycation sites were studied in three dimensional structure of HSA. From the surface electrostatic distribution calculation it was clear that most of the modified lysine residues were situated near the positive or neutral groove. CML modifications by GA were predominantly found in higher electropositive grooves suggesting CML modification requires highly positive local surface environment.

In this context, a fragment ion library for synthetically AML, CML, and CEL modified peptides of albumin by using high resolution accurate mass spectrometer followed with rigorous inspection and validation of MS/MS spectra. Furthermore, using the ion library, AML, CML and CEL modified albumin peptides were quantified by targeted SWATH analysis in the clinical plasma.

The present invention has led to the identification, characterization and quantification of 13 glycated peptides in the clinical diabetic plasma comprising 4-AML, 7-CML and 2-CEL modification representing 9 lysine sites of albumin (K36, K88, K160, K161, K183, K375, K438, K490 and K549). Amongst these sites K549, K438, K490, K88 and K375 were highly sensitive for glycation modification as they had both AML and CML modifications and K549 had additional CEL modification. While K375 (m/z 886.4) showed the highest significant fold change in prediabetes and diabetic plasma. Although it is intriguing that only one lysine site i.e. K549 was found to be CEL modified, this result strongly supports a recent study where no CEL modified peptide was identified.

The development of fragment ion library for AML, CML and CEL modified peptides of albumin will be very useful for quantification of AGE modified peptides of albumin by targeted mass spectrometric approaches. Using this fragment ion library novel AGE modified peptides were quantified. Precursor ions appertaining to K549, K438, K490, K88, K549 could serve as potential novel markers for assessing the degree of glycation or diabetic glycemic status in general and m/z 645.8 (K$^{AML}$*QTALVELVK), m/z 593.8 (K$^{CML}$*QTALVELVK), m/z 600.8 (K$^{CEL}$*QTALVELVK), m/z 601.3 (K$^{AML}$*VPQVSTPTLVEVSR), m/z 528.3 (K$^{CML}$*VPQVSTPTLVEVSRNLGK), m/z 834.6 (MPC*AEDYLSVVLNQLC*VLHEK$^{AML}$*TPVSDR), m/z 808.6 (MPC*AEDYLSVVLNQLC*VLHEK$^{CML}$*TPVSDR), m/z 665.5 (TC*VADESAENC*DK$^{AML}$*SLHTLFGDK), m/z 639.5 (TC*VADESAENC*DK$^{CML}$*SLHTLFGDK), m/z 886.4 (QNC*ELFEQLGEYK$^{CML}$*FQNALLVR) in particular.

Advantages of the Invention

The present fragment ion library established specific to AML, CML and CEL modified peptides of human serum albumin is useful for quantification of AGE modified peptides of albumin by targeted mass spectrometric approaches.

The peptides involving these lysine sites can be potential novel markers to assess the degree of glycation in diabetes.

Precursor ions appertain to K549, K438, K490, K88, K549 could serve as potential novel markers for assessing the degree of glycation or diabetic glycemic status in general.

TABLE 1

Diagnostic fragment ion library for AML, CML and CEL peptides of albumin

| No | Modified site | Peptide start-end | AGE-modified peptide sequence | Peptide MH + Da | Monoisotopic m/z Da (mmu/ppm) | CS | RT | XC | MC | Type of Glycation | Diagnostic fragment ions | | | | | |
|---|---|---|---|---|---|---|---|---|---|---|---|---|---|---|---|---|
| Glucose induced glycation modifications |
| 1 | 490 | 470-496 | MPC*AEDYLSVVLNQ LC*VLHEK*TPVSDR | 3231.54702 | 808.64 (−0.35/−0.43) | +4 | 32.61 | 5.36 | 1 | CML | 674.34 [y6+] 704.23 [b6+] | 860.44 [y8+] 980.38 [b8+] | 989.48 [y10+] 1067.41 [b10+] | 1239.62 [y10+] 1166.48 |
| 2 | 183 | 169-184 | RHPYFYAPELLFFAK*R | 2113.09951 | 529.03 (−0.59/−1.11) | +4 | 27.16 | 4.82 | 2 | CML | 175.11 [y1+] | 726.39 [b9+] | 839.47 [b10+] | 952.56 [y7+] |
| 3 | 490 | 469-496 | RMPC*AEDYLSVVLN QLC*VLHEK*TPVSDR | 3387.64687 | 847.66 (−0.67/−0.79) | +4 | 31.43 | 4.05 | 2 | CML | 573.34 [y5+] 288.14 [b2+] | 989.48 [y8+] 860.44 [b7+] | 1239.62 [y10+] 1023.40 [b10+] | 1498.72 [y12+] 1223.50 |
| 4 | 337 | 311-341 | SHC*IAEVENDEMPA DLPSLAADFVESK*DV C*K | 3534.57338 | 884.39 (+0.57/+0.64) | +4 | 27.78 | 3.98 | 1 | CML | 521.23 [y4+] | 707.33 [y5+] | 923.41 [y7+] | 1355.61 [y11+] |
| 5 | 183 | 170-184 | HPYFYAPELLFFAK*R | 1957.00174 | 653.00 (+0.33/+0.51) | +3 | 28.86 | 3.66 | 1 | CML | 175.11 [y1+] 235.11 [b2+] | 726.39 [y5+] 545.25 [b4+] | 839.47 [y6+] 708.31 [b5+] | 952.56 [y7+] 779.35 [b6+] |
| 6 | 426 | 414-434 | QNC*ELFEQLGEYK*F QNALLVR | 2657.30820 | 886.44 (+1.76/+1.99) | +3 | 28.13 | 3.61 | 1 | AML | 960.56 [y8+] | 1146.66 [y9+] | 1309.72 [y10+] | 1495.78 [y12+] |
| 7 | 337 | 311-341 | SHC*IAEVENDEMPA DLPSLAADFVESK*DV C*K | 3638.61074 | 910.40 (−1.93/−2.12) | +4 | 27.03 | 3.60 | 1 | CML | 521.23 [y4+] | 300.15 [y6 3+] | 1388.60 [y10+] | 1459.64 [y11+] |
| 8 | 438 | 438-452 | K*VPQYSTPTLVEVSR | 1697.94284 | 566.65 (−0.15/−0.27) | +3 | 19.35 | 3.53 | 1 | CML | 187.10 [b1+] | 511.28 [b4+] | 610.35 [b5+] | 798.43 [b7+] |
| 9 | 549 | 549-558 | K*QTALVELVK | 1186.70268 | 593.85 (−0.77/−1.29) | +2 | 18.97 | 3.46 | 1 | CML | 187.10 [b1+] | 600.33 [b5+] | 699.40 [b6+] | 828.44 [b7+] |
| 10 | 88 | 88-109 | TC*VADESAENC*DK* SLHTLFGDK | 2555.09878 | 639.53 (−0.95/−1.48) | +4 | 19.86 | 3.39 | 1 | CML | 1017.53 [y9+] | 1203.62 [y10+] | 1318.66 [y11+] | 385.39 [b13 4+] |
| 11 | 490 | 470-496 | MPC*AEDYLSVVLNQ LC*VLHEK*TPVSDR | 3335.59267 | 834.65 (−0.77/−0.93) | +4 | 31.89 | 3.10 | 1 | AML | 674.34 [y6+] | 274.12 [y8 4+] | 1343.66 [y11+] | 1442.73 [y11+] |
| 12 | 88 | 88-109 | TC*VADESAENC*DK* SLHTLFGDK | 2659.15249 | 665.54 (−0.88/−1.33) | +4 | 18.87 | 2.96 | 1 | AML | 821.87 [b13 2+] | 921.87 [b15 2+] | 948.91 [y15 2+] | 1114.48 [y18 2+] |
| Glyoxylic acid induced glycation modifications |
| 1 | 160 | 139-168 | LVRPEVDVMC*TAFH DNEETFLK*KYLYEIAR | 3744.84463 | 936.96 (+1.11/+1.19) | +4 | 29.34 | 7.33 | 2 | CML | 927.49 [y7+] | 1055.58 [y8+] | 1241.68 [y9+] | 1602.88 [y12+] |
| 2 | 160 & 161 | 139-168 | LVRPEVDVMC*TAFH DNEETFLK*K*YLYEI AR | 3802.84170 | 951.46 (−0.99/−1.04) | +4 | 29.83 | 6.67 | 2 | CML | 927.49 [y7+] | 1299.69 [y9+] | 1412.77 [y10+] | 1789.93 [y13+] |
| 3 | 402 | 397-434 | VFDEFK*PLVEEPQNL IKQNC*ELFEQLGEYK FQNALLVR | 4683.37995 | 937.48 (−0.12/−0.13) | +5 | 33.42 | 6.33 | 2 | CML | 638.28 [b5+] | 921.43 [b7+] | 1133.58 [b9+] | 1262.63 [b10+] |

TABLE 1-continued

Diagnostic fragment ion library for AML, CML and CEL peptides of albumin

| No | Modified site | Peptide start-end | AGE-modified peptide sequence | Peptide MH + Da | Monoisotopic m/z Da (mmu/ppm) | CS | RT | XC | MC | Type of Glycation | Diagnostic fragment ions | | |
|---|---|---|---|---|---|---|---|---|---|---|---|---|---|
| 4 | 183 | 169-184 | RHPYFYAPELLFFAK*R | 2113.09842 | 705.03 (−1.15/−1.63) | +3 | 27.02 | 5.92 | 2 | CML | 175.11 [$y_1^+$] | 726.39 [$y_5^+$] 839.47 [$y_6^+$] | 1178.65 [$y_9^+$] |
| 5 | 437 | 435-452 | YTK*KVPQVSTPTLVE VSR | 2090.14560 | 697.38 (−1.22/−1.75) | +3 | 18.55 | 4.90 | 2 | CML | 554.28 [$b_4^+$] | 701.35 [$b_5^+$] 864.41 [$b_6^+$] | 1274.63 [$b_{10}^+$] |
| 6 | 437 & 438 | 435-452 | YTK*K*VPQVSTPTLV EVSR | 2148.14902 | 716.72 (−1.91/−2.67) | +3 | 19.01 | 4.70 | 2 | CML | 265.11 [$b_2^+$] | 226.11 [$b_3^{2+}$] 579.31 [$b_4^+$] | 678.38 [$b_5^+$] |
| 7 | 438 | 438-456 | K*VPQVSTPTLVEVSR NLGK | 2110.18496 | 528.30 (−0.45/−0.84) | +4 | 21.49 | 4.67 | 2 | CML | 265.11 [$b_2^+$] | 226.11 [$b_3^{2+}$] 637.31 [$b_4^+$] | 736.38 [$b_5^+$] |
| | | | | | | | | | | | 286.17 [$b_2^+$] | 511.28 [$b_4^+$] | 798.44 [$b_7^+$] |
| 8 | 438 | 438-452 | K*VPQVSTPTLVEVSR | 1697.94413 | 566.65 (+0.28/+0.49) | +3 | 19.27 | 4.09 | 1 | CML | 674.39 [$y_6^+$] | 773.46 [$y_7^+$] 902.50 [$y_8^+$] | 1001.57 [$y_9^+$] |
| 9 | 183 | 170-184 | HPYFYAPELLFFAK*R | 1956.99973 | 653.00 (−0.34/−0.52) | +3 | 28.80 | 4.51 | 1 | CML | 187.10 [$b_1^+$] | 383.26 [$b_3^+$] 511.28 [$b_4^+$] | 610.35 [$b_5^+$] |
| | | | | | | | | | | | 589.33 [$y_5^+$] | 702.41 [$y_6^+$] 803.46 [$y_7^+$] | 900.51 [$y_8^+$] |
| 10 | 236 | 230-242 | FGERAFK*AWAVAR | 1566.81462 | 783.91 (−1.52/−1.94) | +2 | 20.40 | 4.19 | 2 | CML | 175.11 [$y_1^+$] | 432.25 [$y_3^+$] 579.32 [$y_4^+$] | 726.39 [$y_5^+$] |
| 11 | 426 | 414-434 | QNC*ELFEQLGEYK*F QNALLVR | 2657.30143 | 886.43 (−0.50/−0.56) | +3 | 28.08 | 4.00 | 1 | CML | 894.44 [$b_7^+$] | 965.48 [$b_8^+$] 859.47 [$y_7^+$] | 1006.54 [$y_8^+$] |
| | | | | | | | | | | | 960.56 [$y_8^+$] | 1146.66 [$y_9^+$] 1309.72 [$y_{10}^+$] | 1495.78 [$y_{12}^+$] |
| 12 | 549 | 549-558 | K*QTALVELVK | 1186.70354 | 593.85 (−0.34/−0.57) | +2 | 18.85 | 3.48 | 1 | CML | 187.10 [$b_1^+$] | 315.16 [$b_2^+$] 600.33 [$b_5^+$] | 699.40 [$b_6^+$] |
| 13 | 229 | 224-233 | C*ASLQK*FGER | 1253.59375 | 418.53 (−0.20/−0.48) | +3 | 13.97 | 2.43 | 1 | CML | 508.25 [$y_4^+$] | 694.35 [$y_5^+$] 822.41 [$y_6^+$] | 935.49 [$y_7^+$] |

TABLE 1-continued

Diagnostic fragment ion library for AML, CML and CEL peptides of albumin

Methylglyoxal induced glycation modifications

| No | Modified site | Peptide start-end | AGE-modified peptide sequence | Peptide MH + Da | Monoisotopic m/z Da (mmu/ppm) | CS | RT | XC | MC | Type of Glycation | Diagnostic fragment ions | | |
|----|---------------|-------------------|-------------------------------|-----------------|-------------------------------|----|----|----|----|-------------------|--------------------------|---|---|
| 1 | 543 | 509-545 | RPC*FSALEVDETYVPKEFNAETFTFHADIC*TLSEK*ER | 4509.12122 | 902.62 (+3.94/+4.37) | +5 | 26.77 | 6.13 | 2 | CEL | 304.16 [y₂⁺] | 504.27 [y₃⁺] | 720.35 [y₅⁺] | 1094.51 [y₈⁺] |
| 2 | 183 | 169-184 | RHPYFYAPELLFFAK*R | 2127.11709 | 532.53 (−0.11/−0.20) | +4 | 27.21 | 5.58 | 2 | CEL | 175.11 [y₁⁺] | 375.23 [y₂⁺] | 593.34 [y₄⁺] | 740.40 [y₅⁺] |
| 3 | 490 | 469-496 | RMPC*AEDYLSVVLNQLC*VLHEK*TPVSDR | 3401.67127 | 681.14 (+1.22/+1.79) | +5 | 31.37 | 5.46 | 2 | CEL | 573.29 [y₇⁺] | 874.46 [y₈⁺] | 1140.56 [y₉⁺] | 1253.64 [y₁₀⁺] |
| 4 | 426 | 414-434 | QNC*ELFEQLGEYK*FQNALLVR | 2671.31943 | 891.11 (+0.29/+0.32) | +3 | 28.15 | 5.26 | 1 | CEL | 960.56 [y₈⁺] | 1160.67 [y₉⁺] | 1323.74 [y₁₀⁺] | 1509.80 [y₁₂⁺] |
| 5 | 97 | 89-105 | SLHTLFGDK*LC*TVATLR | 2004.05752 | 501.76 (−0.21/−0.42) | +4 | 24.04 | 4.48 | 1 | CEL | 871.43 [b₈⁺] | 1071.54 [b₉⁺] | 592.81 [b₁₀²⁺] | 395.54 [b₁₀³⁺] |
| 6 | 438 | 438-452 | K*VPQVSTPTLVEVSR | 1711.95920 | 571.32 (+0.08/+0.15) | +3 | 19.37 | 4.04 | 1 | CEL | 201.12 [b₁⁺] | 300.19 [b₂⁺] | 525.30 [b₄⁺] | 624.37 [b₅⁺] |
| 7 | 549 | 549-558 | K*QTALVELVK | 1200.71855 | 600.86 (−0.66/−1.10) | +2 | 19.12 | 3.90 | 1 | CEL | 201.12 [b₁⁺] | 329.18 [b₂⁺] | 614.35 [b₅⁺] | 842.46 [b₇⁺] |
| 8 | 183 | 170-184 | HPYFYAPELLFFAK*R | 1971.01664 | 657.67 (+0.08/+0.12) | +3 | 28.99 | 3.43 | 1 | CEL | 175.11 [y₁⁺] | 375.23 [y₂⁺] | 740.40 [y₅⁺] | 853.49 [y₆⁺] |
| 9 | 598 | 598-609 | K*LVAASQAALGL | 1213.71477 | 607.36 (−0.18/−0.30) | +2 | 21.30 | 3.20 | 1 | CEL | 235.11 [b₂⁺] | 545.25 [y₂⁺] | 708.31 [b₅⁺] | 1005.44 [b₈⁺] 841.47 [b₈⁺] |
| 10 | 36 | 35-44 | FK*DLGEENFK | 1298.62470 | 433.54 (−0.56/−1.29) | +3 | 16.26 | 2.62 | 1 | CEL | 201.12 [b₁⁺] 148.07 [b₁⁺] | 484.31 [b₄⁺] 348.19 [b₂⁺] | 770.44 [b₇⁺] 463.21 [b₃⁺] | 633.32 [b₅⁺] |

Static modification:
*Carbamidomethyl (57.02146 Da),
CS—Charge state,
RT—Retention time,
XC—Xcorr,
MC—Missed cleavage Sequence of human serum albumin SEQ ID No. 1

MKWVTFISLLFLFSSAYSRGVFRRDAHKSEVAHRFKDLGEENFKALVLIA

FAQYLQQCPFEDHVKLVNEVTEFAKTCVADESAENCDKSLHTLFGDKLCT

VATLRETYGEMADCCAKQEPERNECFLQHKDDNPNLPRLVRPEVDVMCTA

FHDNEETFLKKYLYEIARRHPYFYAPELLFFAKRYKAAFTECCQAADKAA

CLLPKLDELRDEGKASSAKQGLKCASLQKFGERAFKAWAVARLSQRFPKA

EFAEVSKLVTDLTKVHTECCHGDLLECADDRADLAKYICENQDSISSKLK

ECCEKPLLEKSHCIAEVENDEMPADLPSLAADFVGSKDVCKNYAEAKDVF

LGMFLYEYARRHPDYSVVLLLRLAKTYETTLEKCCAAADPHECYAKVFDE

FKPLVEEPQNLIKQNCELFEQLGEYKFQNALLVRYTKKVPQVSTPTLVEV

SRNLGKVGSKCCKHPEAKRMPCAEDCLSVFLNQLCVLHEKTPVSDRVTKC

CTESLVNGRPCFSALEVDETYVPKEFNAETFTFHADICTLSEKERQIKKQ

TALVELVKHKPKATKEQLKAVMDDFAAFVEKCCKADDKETCFAEEGKKLV

AASQAALGL

The above sequence depicts the amino acid sequence of human serum albumin
length of the sequence: 609
It is naturally occurring.

---

SEQUENCE LISTING

<110> CSIR, IN
<120> An in vitro process for the identification and quantification
      of carboxymethyl and carboxyethyl level of albumin in a sample
<130> 0221NF2015
<160> 1
<170> PatentIn version 3.5
<210> 1
<211> 609
<212> PRT
<213> Homo sapiens
<400> 1

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
130                 135                 140                 145

Asp Val Met Cys Thr Ala Phe His Asp Asn Glu Glu Thr Phe Leu Lys
                150                 155                 160

Lys Tyr Leu Tyr Glu Ile Ala Arg Arg His Pro Tyr Phe Tyr Ala Pro
            165                 170                 175

Glu Leu Leu Phe Phe Ala Lys Arg Tyr Lys Ala Ala Phe Thr Glu Cys
        180                 185                 190

Cys Gln Ala Ala Asp Lys Ala Ala Cys Leu Leu Pro Lys Leu Asp Glu
    195                 200                 205

Leu Arg Asp Glu Gly Lys Ala Ser Ser Ala Lys Gln Gly Leu Lys Cys
210                 215                 220                 225

Ala Ser Leu Gln Lys Phe Gly Glu Arg Ala Phe Lys Ala Trp Ala Val
                230                 235                 240

Ala Arg Leu Ser Gln Arg Phe Pro Lys Ala Glu Phe Ala Glu Val Ser
            245                 250                 255

SEQUENCE LISTING

```
Lys Leu Val Thr Asp Leu Thr Lys Val His Thr Glu Cys Cys His Gly
        260                 265                 270

Asp Leu Leu Glu Cys Ala Asp Asp Arg Ala Asp Leu Ala Lys Tyr Ile
    275                 280                 285

Cys Glu Asn Gln Asp Ser Ile Ser Ser Lys Leu Lys Glu Cys Cys Glu
290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Gly Ser
            325                 330                 335

Lys Asp Val Cys Lys Asn Tyr Ala Glu Ala Lys Asp Val Phe Leu Gly
                340                 345                 350

Met Phe Leu Tyr Glu Tyr Ala Arg Arg His Pro Asp Tyr Ser Val Val
    355                 360                 365

Leu Leu Leu Arg Leu Ala Lys Thr Tyr Glu Thr Thr Leu Glu Lys Cys
370                 375                 380                 385

Cys Ala Ala Ala Asp Pro His Glu Cys Tyr Ala Lys Val Phe Asp Glu
            390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
    420                 425                 430

Val Arg Tyr Thr Lys Lys Val Pro Gln Val Ser Thr Pro Thr Leu Val
    435                 440                 445

Glu Val Ser Arg Asn Leu Gly Lys Val Gly Ser Lys Cys Cys Lys His
450                 455                 460                 465

Pro Glu Ala Lys Arg Met Pro Cys Ala Glu Asp Cys Leu Ser Val Phe
                470                 475                 480

Leu Asn Gln Leu Cys Val Leu His Glu Lys Thr Pro Val Ser Asp Arg
            485                 490                 495

Val Thr Lys Cys Cys Thr Glu Ser Leu Val Asn Gly Arg Pro Cys Phe
        500                 505                 510

Ser Ala Leu Glu Val Asp Glu Thr Tyr Val Pro Lys Glu Phe Asn Ala
    515                 520                 525

Glu Thr Phe Thr Phe His Ala Asp Ile Cys Thr Leu Ser Glu Lys Glu
530                 535                 540                 545

Arg Gln Ile Lys Lys Gln Thr Ala Leu Val Glu Leu Val Lys His Lys
                550                 555                 560

Pro Lys Ala Thr Lys Glu Gln Leu Lys Ala Val Met Asp Asp Phe Ala
            565                 570                 575

Ala Phe Val Glu Lys Cys Cys Lys Ala Asp Asp Lys Glu Thr Cys Phe
        580                 585                 590

Ala Glu Glu Gly Lys Lys Leu Val Ala Ala Ser Gln Ala Ala Leu Gly
    595                 600                 605

Leu
609
```

SEQUENCE LISTING

<160> NUMBER OF SEQ ID NOS: 1

<210> SEQ ID NO 1
<211> LENGTH: 609
<212> TYPE: PRT
<213> ORGANISM: Homo sapiens

<400> SEQUENCE: 1

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Gly Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Gly Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

-continued

```
Leu Leu Leu Arg Leu Ala Lys Thr Tyr Glu Thr Thr Leu Glu Lys Cys
    370             375             380

Cys Ala Ala Ala Asp Pro His Glu Cys Tyr Ala Lys Val Phe Asp Glu
385             390             395                 400

Phe Lys Pro Leu Val Glu Glu Pro Gln Asn Leu Ile Lys Gln Asn Cys
            405             410                 415

Glu Leu Phe Glu Gln Leu Gly Glu Tyr Lys Phe Gln Asn Ala Leu Leu
            420             425             430

Val Arg Tyr Thr Lys Lys Val Pro Gln Val Ser Thr Pro Thr Leu Val
        435             440             445

Glu Val Ser Arg Asn Leu Gly Lys Val Gly Ser Lys Cys Cys Lys His
    450             455             460

Pro Glu Ala Lys Arg Met Pro Cys Ala Glu Asp Cys Leu Ser Val Phe
465             470             475             480

Leu Asn Gln Leu Cys Val Leu His Glu Lys Thr Pro Val Ser Asp Arg
            485             490             495

Val Thr Lys Cys Cys Thr Glu Ser Leu Val Asn Gly Arg Pro Cys Phe
            500             505             510

Ser Ala Leu Glu Val Asp Glu Thr Tyr Val Pro Lys Glu Phe Asn Ala
            515             520             525

Glu Thr Phe Thr Phe His Ala Asp Ile Cys Thr Leu Ser Glu Lys Glu
            530             535             540

Arg Gln Ile Lys Lys Gln Thr Ala Leu Val Glu Leu Val Lys His Lys
545             550             555             560

Pro Lys Ala Thr Lys Glu Gln Leu Lys Ala Val Met Asp Asp Phe Ala
            565             570             575

Ala Phe Val Glu Lys Cys Cys Lys Ala Asp Asp Lys Glu Thr Cys Phe
            580             585             590

Ala Glu Glu Gly Lys Lys Leu Val Ala Ala Ser Gln Ala Ala Leu Gly
            595             600             605

Leu
```

I claim:

1. An in vitro process for the identification, quantification or identification and quantification of carboxymethyl and carboxyethyl level of albumin in a sample comprising:
   (a) establishing a diagnostic fragment ion library for advanced glycation end-product (AGE), wherein the AGE comprises carboxymethyl lysine (CML), and carboxyethyl lysine (CEL) modified peptides and wherein the fragment ion library is specific to modified carboxymethyl and carboxyethyl glycated sites selected from the group consisting of K36, K88, K160, K161, K183, K375, K438, K490 and K549 in SEQ ID NO: 1, comprising:
      (i) modifying human serum albumin (HSA) with glucose, glycoxylic acid, or methyl glyoxal to form AGE modified peptides;
      (ii) subjecting the AGE to tryptic digestion;
      (iii) manually validating the AGE modified peptides for consensus MS and MS/MS spectra; and
      (iv) constructing the diagnostic library for CML and CEL peptides of albumin;
   (b) obtaining a sample from a subject;
   (c) generating fragment ions from the sample via mass spectrometry;
   (d) identifying the specificity of fragment ions obtained in step (c);
   (e) comparing the fragment ions identified in step (d) to the ion library established in step (a); and
   (f) quantifying the levels of CML and CEL modified peptide content of fragment ions obtained in step (c), wherein AGE modified glycation sites are situated at lysine (K) residues
   (g) determining if a patient has a normal glucose tolerance, an impaired glucose tolerance, is a microalbuminuria, or is a diabetic.

2. The process as claimed in claim 1, wherein AGE modified glycated sites are identified and quantified in human serum albumin represented by amino acid sequence having at least 80% similarity with SEQ ID NO: 1.

3. The process as claimed in claim 1, wherein AGE modified glycated sites are selected from the group consisting of K438 and K490.

4. A method for employing a diagnostic kit for identifying the extent of diabetes in a diseased individual comprising;
   (i) obtaining a sample of serum from a subject;
   (ii) subjecting the serum to fragmentation by mass spectrometry;
   (iii) identifying, quantifying, or identifying and quantifying carboxymethyl and carboxyethyl level of albumin in the withdrawn sample;
   (iv) establishing a diagnostic fragment ion library for advanced glycation end-product (AGE), wherein the AGE comprises carboxymethyl lysine (CMF), and carboxyethyl lysine (CEE) modified peptides and wherein the fragment ion library is specific to modified carboxymethyl and carboxyethyl glycated sites selected from the group consisting of K36, K88, K160, K161, K183, K375, K438, K490 and K549 in SEQ ID NO: 1;

(v) comparing the carboxymethyl and carboxyethyl level of albumin from step (iii) with the diagnostic fragment ion library specific to carboxymethyl and carboxyethyl modified glycated sites selected from the group consisting of K36, K88, K160, K161, K183, K375, K438, K490, and K549 in SEQ ID NO: 1; and (vi) classifying the subject as normal glucose tolerance, microalbuminuria, pre-diabetic impaired glucose tolerance, or diabetic.

5. The method of claim 4 wherein the sample of serum is obtained using a minimally invasive sterilized device.

* * * * *